United States Patent [19]
Wilson

[11] Patent Number: 5,358,476
[45] Date of Patent: * Oct. 25, 1994

[54] BREAST PUMP ADAPTER FOR FILLING INFANT NURSERS HAVING DISPOSABLE LINERS AND METHODS OF OPERATION

[75] Inventor: Michael J. Wilson, Vancouver, Canada

[73] Assignee: Aurora Search Ltd., Delta, Canada

[*] Notice: The portion of the term of this patent subsequent to Aug. 21, 2007 has been disclaimed.

[21] Appl. No.: 12,165

[22] Filed: Jan. 28, 1993

Related U.S. Application Data

[63] Continuation-in-part of Ser. No. 746,661, Aug. 19, 1991, abandoned.

[30] Foreign Application Priority Data

Aug. 17, 1990 [CA] Canada ................. 2023580

[51] Int. Cl.⁵ ............................................. A61M 1/00
[52] U.S. Cl. ..................................................... 604/74
[58] Field of Search ........................... 604/74–76, 604/313, 316, 346; 215/11.5

[56] References Cited

U.S. PATENT DOCUMENTS

| | | | |
|---|---|---|---|
| 3,911,920 | 10/1975 | Susinn . | |
| 4,238,040 | 12/1980 | Fitzpatrick | 215/11 |
| 4,673,388 | 6/1987 | Schlensog et al. | 604/74 |
| 4,680,028 | 7/1987 | Stuart | 604/74 |
| 4,759,747 | 7/1988 | Aida et al. | 604/74 |
| 4,813,932 | 3/1989 | Hobbs | 604/74 |
| 4,857,051 | 8/1989 | Larsson | 604/74 |
| 4,892,517 | 1/1990 | Yuan et al. | 604/74 |
| 4,929,229 | 5/1990 | Larsson | 604/74 |
| 4,950,236 | 8/1990 | Wilson | 604/74 |
| 5,009,638 | 4/1991 | Riedweg et al. | 604/74 |
| 5,071,403 | 12/1991 | Larsson | 604/74 |

FOREIGN PATENT DOCUMENTS 968660 6/1975 Canada ................. 604/74

*Primary Examiner*—Ralph Lewis
*Attorney, Agent, or Firm*—Nixon & Vanderhye

[57] ABSTRACT

Infant nursers use a disposable, flexible plastic liner in a rigid, reusable shell. An adapter allows the breast milk to be pumped directly into the liner of the nurser without the need for any moving parts in response to cyclic pressure variations in the reservoir of the adapter. The adapter snaps onto the nipple-retaining cap and uses the liner of the nurser itself to form a valve. In a second embodiment, the adapter is provided with a unitary threaded circular rim to attach directly to the threaded end of the nurser shell. The adapter also includes a trigger for manual actuation of the valve when unmodulated negative pressure is applied to the reservoir.

42 Claims, 12 Drawing Sheets

BREAST PUMP ADAPTER FOR FILLING INFANT NURSERS HAVING DISPOSABLE LINERS AND METHODS OF OPERATION

RELATED APPLICATIONS

This application is a continuation-in-part of application Ser. No. 07/746,661, filed Aug. 19, 1991, now abandoned.

BACKGROUND AND SUMMARY OF THE INVENTION

The present invention relates to breast pumps and more particularly to an adapter for enabling existing breast pumps to fill infant nursers having disposable liners and methods of operation.

The combination of an increased awareness of the health benefits of breast-feeding an infant and the increased number of women returning to the work force shortly after giving birth has led to an increased use of breast pumps for maintaining a supply of breast milk for the infant when the mother is unavailable. Banks of donors' breast milk have also been established to nourish needy infants. A wide variety of types of breast pumps is available, both manual and electrically operated. The most effective breast pumps provide alternating positive and negative pressure at 45 to 60 cycles per minute to simulate the sucking action of the infant. Most such pumps provide a receptacle for temporarily receiving the extracted milk. The milk is then transferred to the baby bottle or to a freezer container for freezing and long-term storage.

Infant nursers, such as those manufactured and sold under the PLAYTEX trademark, consisting of a disposable polyethylene plastic liner fitted inside a rigid, reusable plastic shell, have become very popular due to the convenience and added cleanliness and safety which comes from not having to wash and reuse the baby's bottle. Disposable bags of a nylon/polyethylene laminate have also been developed to reduce the loss of nutrients when the milk is stored over a long period of time. Where the mother wishes to utilize a nurser to feed her own breast milk to her child, it has been necessary for the mother to express the milk by hand into the disposable liner or use a breast pump and transfer the extracted milk by hand from the pump container to the nurser. Both procedures are time-consuming, messy and unsanitary.

One breast pump known to the inventor, disclosed in U.S. Pat. No. 4,705,504, issued Nov. 10, 1987 to Viers, uses a disposable, removable bag to receive the pumped milk, but this design involves using a squeezable rubber bulb to create the negative pumping pressure, and the disposable bag is held onto the rubber bulb by an elastic band. The bag has no rigid support. Consequently, this pump is difficult and inefficient to use and still requires that the user transfer the filled bag of milk to the nurser or some other dispenser.

There is therefore a need for an effective adapter which allows existing breast pumps to be used to fill infant nursers directly.

The present invention provides an adapter for filling infant nursers from a breast pump and methods of operation therefor. The adapter comprises a breast shield adapted to receive a female breast, a storage reservoir communicating at its upper end with and extending downwardly from the shield and substantially closed at its lower end by a surface extending obliquely to the plane normal to the longitudinal direction of the reservoir, and an air inlet communicating with the reservoir for connecting the pump. The air inlet may be shielded by a baffle. According to one embodiment, there is a resilient clip extending from the exterior wall of the reservoir near the upper end thereof and beneath the shield for releasably securing the adapter to the lip of the nipple-retaining cap. The closed end of the reservoir has a groove across its upper portion for seating on the lip of the nipple-retaining cap of the nurser and a hole for the passage of milk. In a second embodiment, the adapter has a threaded circular rim moulded as a unitary part of it, and which threads onto the end of the nurser shell.

In a preferred embodiment according to the present invention, there is provided a method of filling an infant nurser having an adapter and a chamber in the adapter in communication with a breast shield, the nurser further including a rigid shell and a flexible liner within the shell forming a container for storing milk, and a passage through the adapter for communication between the chamber and the flexible container, comprising the steps of applying a first pressure within the chamber in communication with a female breast through the breast shield for expressing milk from the breast into the chamber in response to the application of the first pressure in the chamber, the step of applying the first pressure including applying a negative suction to the chamber to draw a portion of the flexible liner against the adapter to seal the passage, applying a second pressure within the chamber higher than the first pressure to displace the flexible liner portion away from the adapter to enable flow of milk from the chamber through the passage into the flexible container, temporarily storing in the chamber the milk expressed therein during application of the first pressure, flowing the milk from the chamber into the flexible container during application of the second pressure and alternating the pressure applied to the chamber between the first and second pressures.

In a further preferred embodiment according to the present invention, there is provided apparatus for filling infant nursers comprising an infant nurser having a rigid shell and a flexible, liquid-containing liner supported in the rigid shell, an adapter including a breast shield adapted to receive a female breast, means defining a hollow chamber in communication at one end with the shield and substantially closed at its opposite end, the chamber-defining means having a wall portion with an aperture through the wall portion for the passage of milk from the chamber into the liner, means carried by the adapter for connecting a pump in communication with the hollow chamber to produce alternating pressures within the chamber, means carried by the adapter for releasably securing the adapter to the nurser and relative to the flexible liner supported in the nurser whereby the wall portion is placed in sufficiently close proximity to a portion of the flexible liner to cause the liner portion to act as a valve with respect to the aperture, the wall portion including a concave portion about the aperture and in opposition to the liner for facilitating movement of the liner portion toward the aperture into the concave portion to seal the aperture and away from the aperture outwardly of the concave portion to open the aperture in response to the alternating pressures within the chamber and the shell having an end portion, the securing means including an annular cap about the end portion of the shell securing the liner between the shell and the cap with the liner disposed within the shell end portion, the wall portion including a convex portion in general conformance to the curvature of the shell, the concave portion being disposed in the convex portion.

In a still further preferred embodiment according to the present invention, there is provided an adapter as part of a breast pump for filling infant nursers wherein the infant nurser comprises a flexible, liquid-containing liner supported in a rigid shell, the adapter comprising a breast shield adapted to receive a female breast, means defining a hollow chamber in communication at one end with the shield and substantially closed at its opposite end, the chamber-defining means having a wall portion with an aperture through the wall portion for the passage of milk from the chamber into the liner, means carried by the adapter for connecting a pump in communication with the hollow chamber to produce alternating pressures within the chamber and means carried by the adapter for releasably securing the adapter to the nurser and relative to a flexible liner supported in the nurser whereby the wall portion is placed in sufficiently close proximity to a portion of the flexible liner to cause the liner portion to act as a valve with respect to the aperture, the wall portion including a concave portion about the aperture and in opposition to the liner for facilitating movement of the liner portion toward the aperture into the concave portion to seal the aperture and away from the aperture outwardly of the concave portion to open the aperture in response to the alternating pressures within the chamber.

In a still further preferred embodiment according to the present invention, there is provided an adapter as part of a breast pump for filling infant nursers wherein the infant nurser comprises a flexible, liquid-containing liner supported in a rigid shell, the adapter comprising a breast shield adapted to receive a female breast, means defining a hollow chamber in communication at one end with the shield and substantially closed at its opposite end, the chamber-defining means having a wall portion with an aperture through the wall portion for the passage of milk from the chamber into the liner, means carried by the adapter for connecting a pump in communication with the hollow chamber to produce a negative pressure within the chamber, means carried by the adapter for releasably securing the adapter to the nurser and relative to a flexible liner supported in the nurser whereby the wall portion is placed in sufficiently close proximity to a portion of the flexible liner to serve in conjunction with the liner portion as a valve with respect to the aperture and a manual actuator carried by said adapter for actuating said valve.

In a still further preferred embodiment according to the present invention, there is provided apparatus for filling infant nursers comprising an infant nurser having a rigid shell and a flexible, liquid-containing liner supported in the rigid shell, an adapter including a breast shield adapted to receive a female breast, means defining a hollow chamber in communication at one end with the shield and substantially closed at its opposite end, the chamber-defining means having a wall portion with an aperture through the wall portion for the passage of milk from the chamber into the liner, means carried by the adapter for connecting a pump in communication with the hollow chamber to produce alternating pressures within the chamber, means carried by the adapter for releasably securing the adapter to the nurser and relative to the flexible liner supported in the nurser whereby the wall portion is placed in sufficiently close proximity to a portion of the flexible liner to cause the liner portion to act as a valve with respect to the aperture, the wall portion including a concave portion about the aperture and in opposition to the liner shell for facilitating movement of the liner portion toward the aperture into the concave portion to seal the aperture and away from the aperture outwardly of the concave portion to open the aperture in response to the alternating pressures within the chamber, the actuator including a valve closure element movable in response to movement of the actuator into a position for closing the liner portion into sealing engagement about the aperture and the shell having an end portion, the securing means including a threaded cap about the end portion of the shell securing the liner between the shell and the cap with the liner disposed within the shell end portion.

In a still further preferred embodiment of the present invention, there is provided an adapter as part of a breast pump for filling an infant nurser in combination with the infant nurser, comprising a rigid shell having an open end, a flexible liner for containing a liquid and supported within the rigid shell about the open end, a breast shield carried by the adapter for receiving a female breast, means carried by the adapter defining a hollow chamber in communication at one end with the shield and substantially closed at its opposite end, the chamber-defining means having a wall portion with a passage through the wall portion for passing liquid from the chamber into the liner, a pump including a housing and a member movable relative to the housing defining at least in part an expandable and contractable volume within the housing, the volume being in communication with the chamber, means for displacing the member relative to the housing for producing alternating pressures within the chamber, a valve for opening and closing the passage in response to the alternating pressures within the chamber and means carried by the adapter for releasably securing the adapter to the shell adjacent the open end thereof, the adapter and the liner being located relative to one another such that the wall portion and a portion of the flexible liner are located in sufficiently close proximity to one another to cause the flexible liner portion to act as the valve with respect to the passage.

In a still further preferred embodiment according to the present invention, there is provided a breast pump in combination with an infant nurser comprising a generally cylindrical shell having an externally threaded neck portion, a flexible liner disposed in the shell with portions overlapping the neck portion of the shell and the externally threaded portion thereof, an adapter as part of the breast pump for filling the liner with milk including a breast shield adapted to receive a female breast and an opening an the adapter for discharging milk from the adapter into the liner, means including an internally threaded part for cooperation with the externally threaded neck of the shell for releasably securing the adapter, shell and liner to one another, means in communication with the chamber for periodically changing the pressure in the chamber and a valve for opening and closing the opening in response to the changing pressure in the chamber, the adapter opening being located relative to the liner within the shell such that a wall portion of the adapter about the opening is placed in sufficiently close proximity to the flexible liner to cause a portion of the liner to act as a portion of the valve with respect to the adapter opening whereby the liner portion and the wall portion cooperate to open and close the adapter opening.

In a still further preferred embodiment of the present invention, there is provided apparatus for expressing milk from a female breast and storing the milk to facilitate the nursing of an infant, comprising a generally cylindrical shell having an externally threaded neck portion, a flexible liner disposed in the shell with portions overlapping the neck portion of the shell and the external threads thereof, an adapter for filling the liner with milk including a breast shield adapted to receive a female breast and an opening in the adapter for discharging milk from the adapter into the liner, means including an internally threaded part for cooperation with the externally threaded neck of the shell for releasably securing the adapter, shell and liner one to the other, the securing means including a collar carrying the internally threaded part.

Accordingly, it is a primary object of the present invention to provide a novel and improved breast pump adapter for filling nursers having disposable liners and methods of operation including improvements with respect to the breast pump adapter in my prior U.S. Pat. No. 4,950,236, issued Aug. 21, 1990, the disclosure of which is incorporated herein by reference.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to a present preferred embodiment of the invention, an example of which is illustrated in the accompanying drawings.

Figure 1:
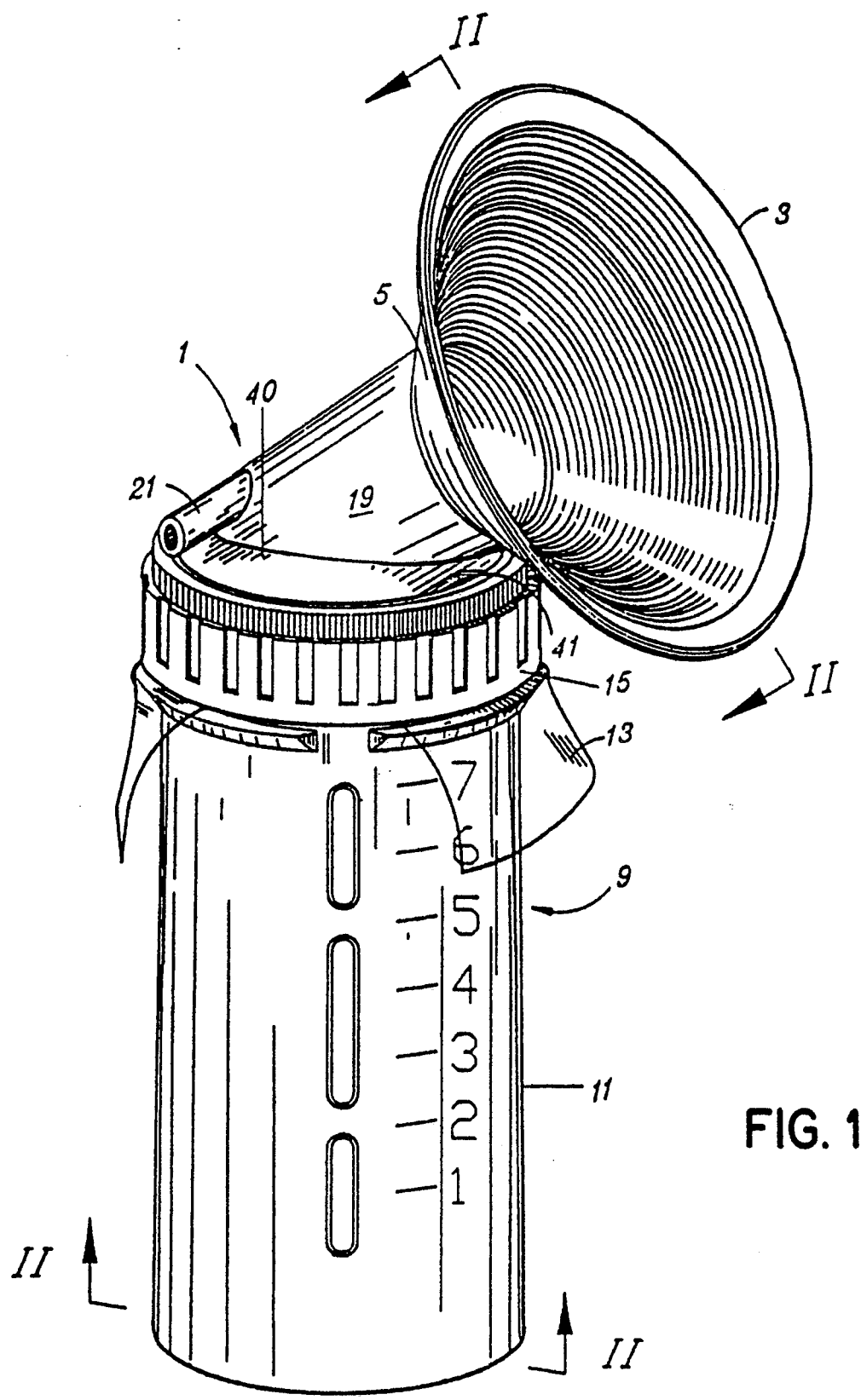
FIG. 1 is a perspective view of a first embodiment of the invention installed on an infant nurser.
Figure 2:
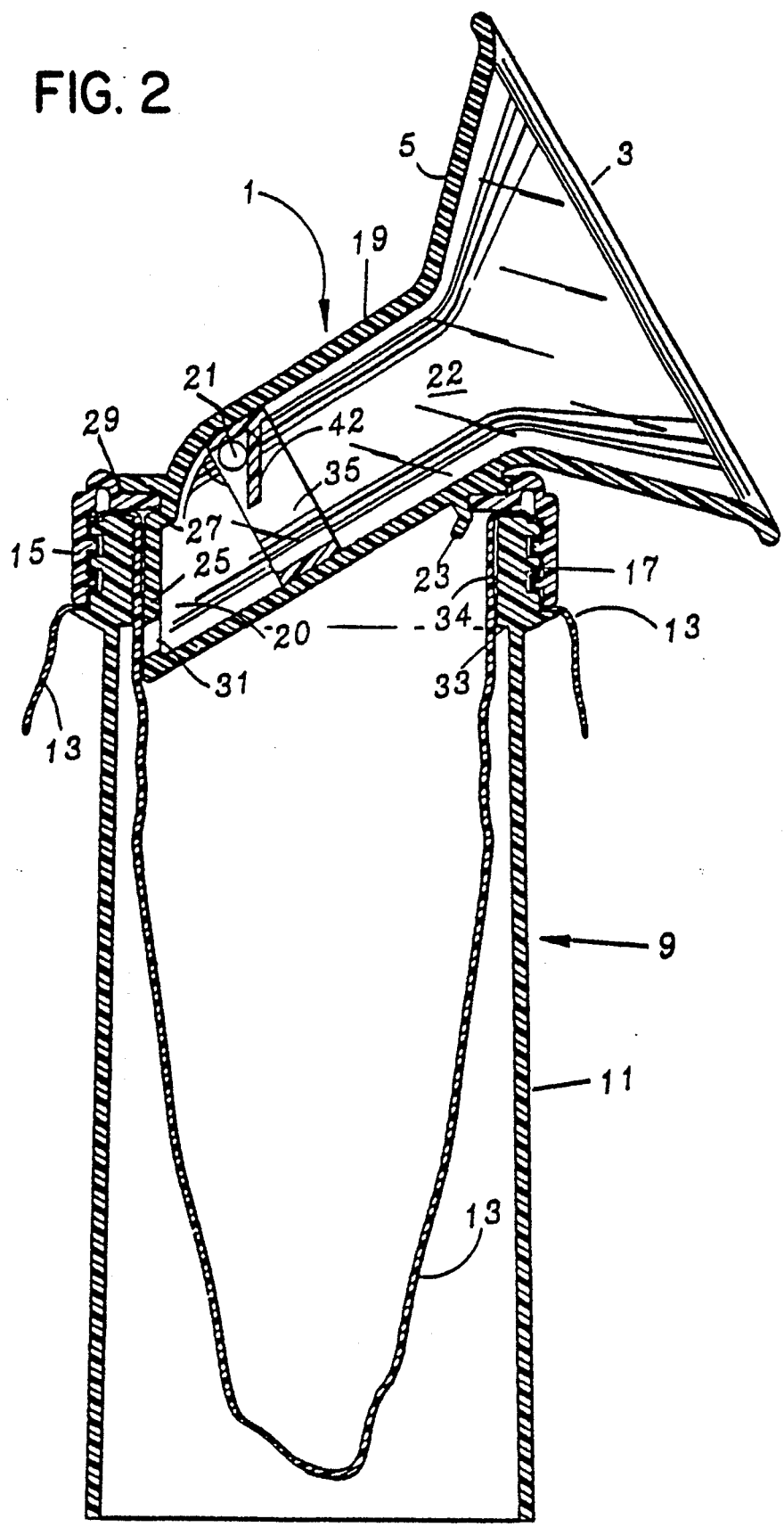
FIG. 2 is a cross-section along lines II—II of FIG. 1.
Figure 4:
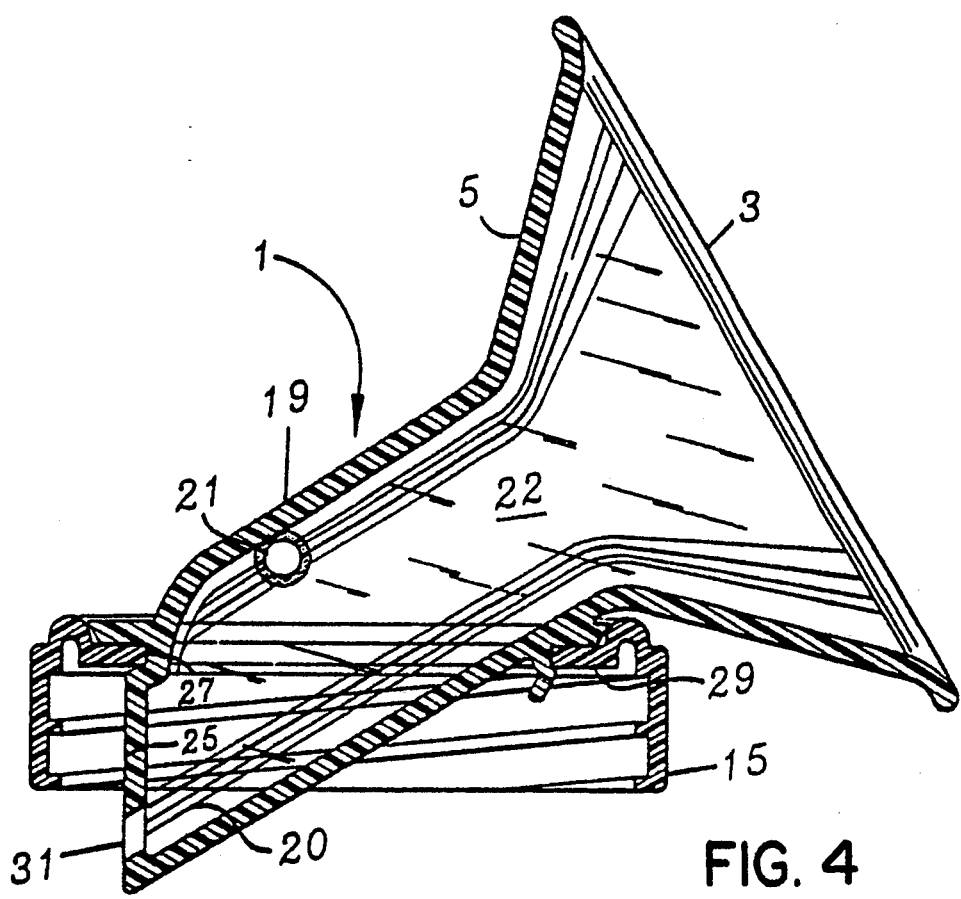
FIG. 4 is a detail of the cross-section of FIG. 2 with nurser and baffle removed and nipple-retaining cap attached.
Figure 3:
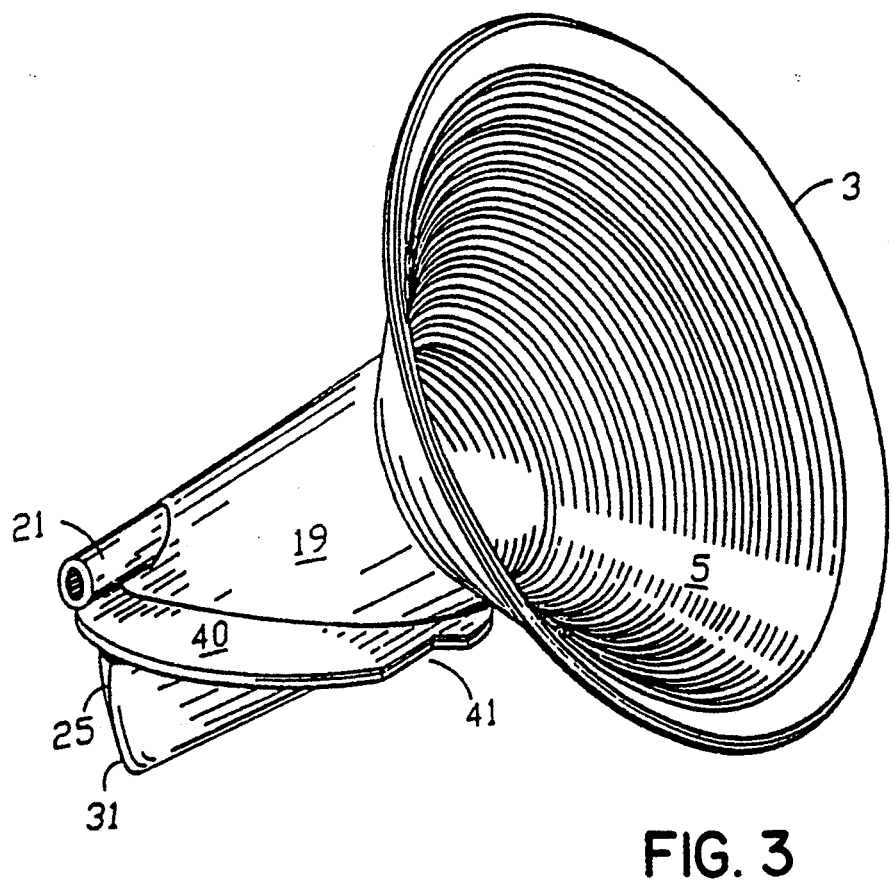
FIG. 3 is a perspective view of the adapter of the invention separated from the nurser.
Figure 5:
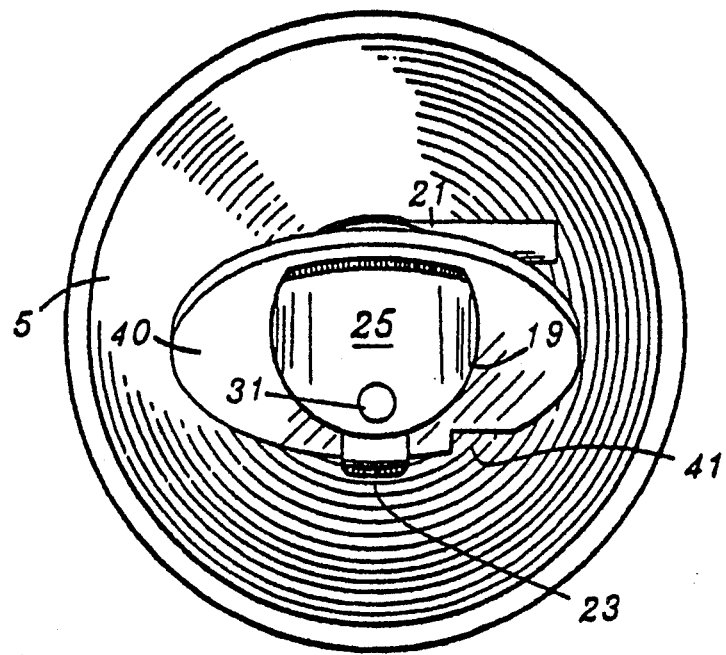
FIG. 5 is a rear view of the adapter shown in FIG. 3.

The adapter of the invention is designated generally by reference numeral 1. It includes a plastic breast shield 3 of existing design which has a conical section 5 which is pressed against the female breast. The adapter is shown in FIGS. 1 and 2 installed on a standard infant nurser 9, such as that sold under the trademark PLAYTEX, which consists of a cylindrical, rigid plastic shell 11 and a disposable liner 13 of flexible polyethylene film. Laminates of nylon and polyethylene are also used for the disposable liner. The bottle has a circular cap 15 which is threaded onto threaded end 17 in the upper outer surface of the shell and normally retains the rubber nipple in the opening of the nurser. The central area of cap 15 is thus open, leaving a horizontally extending annular rim 29. The upper edge of the liner is held in place between the cap 15 and shell 11 when cap 15 is screwed onto threaded end 17 over the liner. Around the inner, upper edge of the shell 11 in such nursers in the area of the threaded end 17, there is an inwardly projecting horizontal ledge 33 meeting inner surface 34.

The adapter has a cylindrical section 19 which forms a lower reservoir section 20 and an upper neck section 22. Projecting horizontally from the upper edge of the reservoir section is a connecting tube 21 to which the pumping source of alternating higher and lower pressure or modulated negative pressure is attached. Projecting downwardly from the lower surface of the upper neck section is a resilient clip 23. A circular cover flange 40 extends horizontally from the cylindrical section 19. This flange covers the open areas of the mouth of the nurser when the adapter is installed to prevent the entry of foreign matter into the milk being collected. It has an opening 41 to allow air to escape from the nurser liner as it is filled.

The lower end of the reservoir 20 is substantially closed off by a curved surface 25 which cuts obliquely across the reservoir section as shown in FIG. 2 so that when surface 25 is parallel to the curved vertical sides of shell 11, the axis of the cylindrical section 19 forms an acute angle with the horizontal. A slot or groove 27 is provided across the upper edge of surface 25 to receive the inner lip 29 of cap 15. A hole 31 is formed in the lower part of the surface 25, typically of about $\frac{1}{8}''$ to $\frac{1}{4}''$ in diameter. The dimension of cylindrical section 19 is chosen so that the hole 31 is located below the ledge 33. Thus, while the flexible liner 13 is in contact with both surface 34 and surface 25 in the area above hole 31, the liner has a slight freedom of movement in the horizontal direction of the vicinity of hole 31. Surface 25 conforms in curvature to that of the shell 11 and has rounded edges to allow the cap 15 to be screwed or unscrewed onto or off of end 17 with the adapter installed on the cap.

Figure 6:
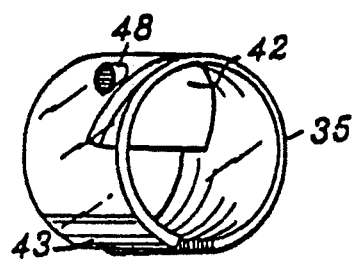
FIG. 6 is a perspective view of the removable baffle insert of the invention.
Figure 7:
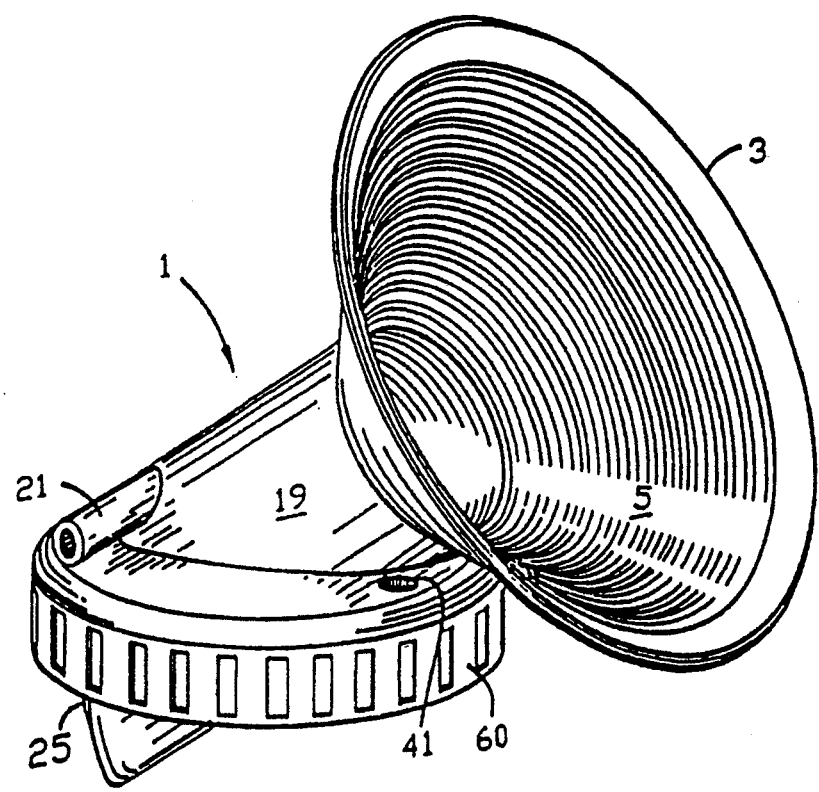
FIG. 7 is a perspective view of a second embodiment of the invention.
Figure 8:
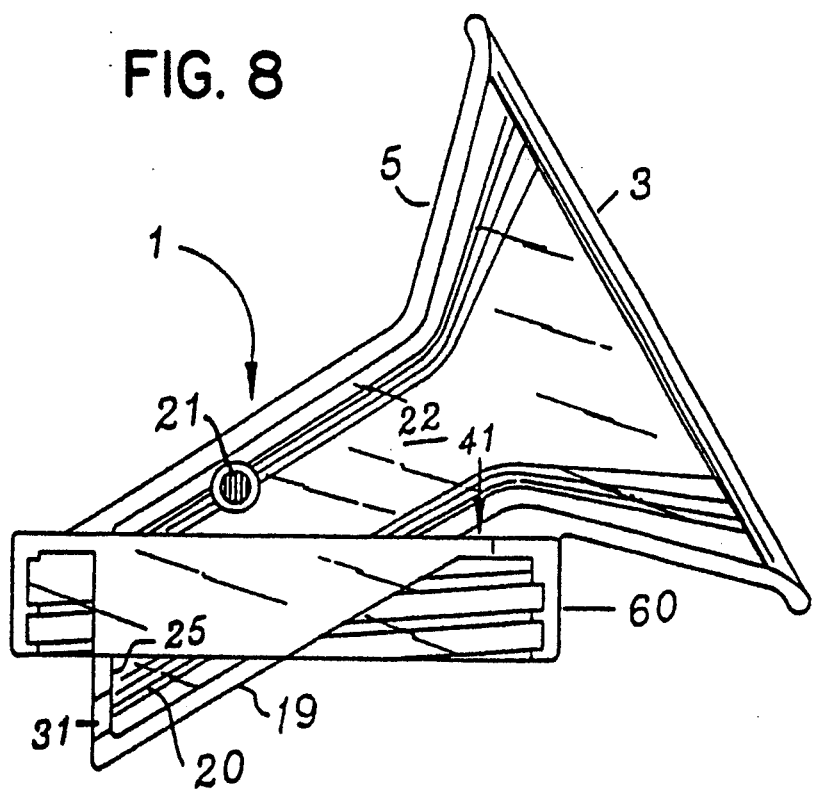
FIG. 8 is a side view of the embodiment shown in FIG. 7.
Figure 10:
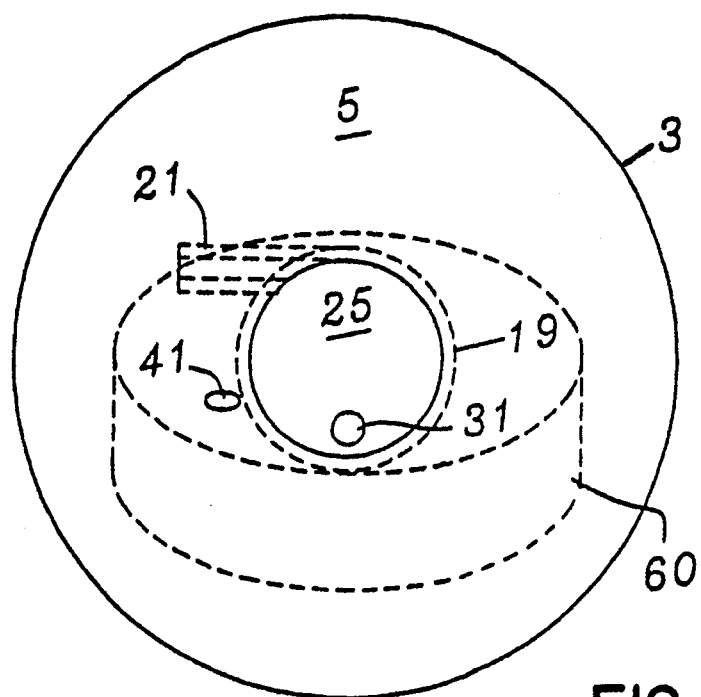
FIG. 10 is a plan view looking into the breast shield of the adapter shown in FIG. 7.
Figure 9:
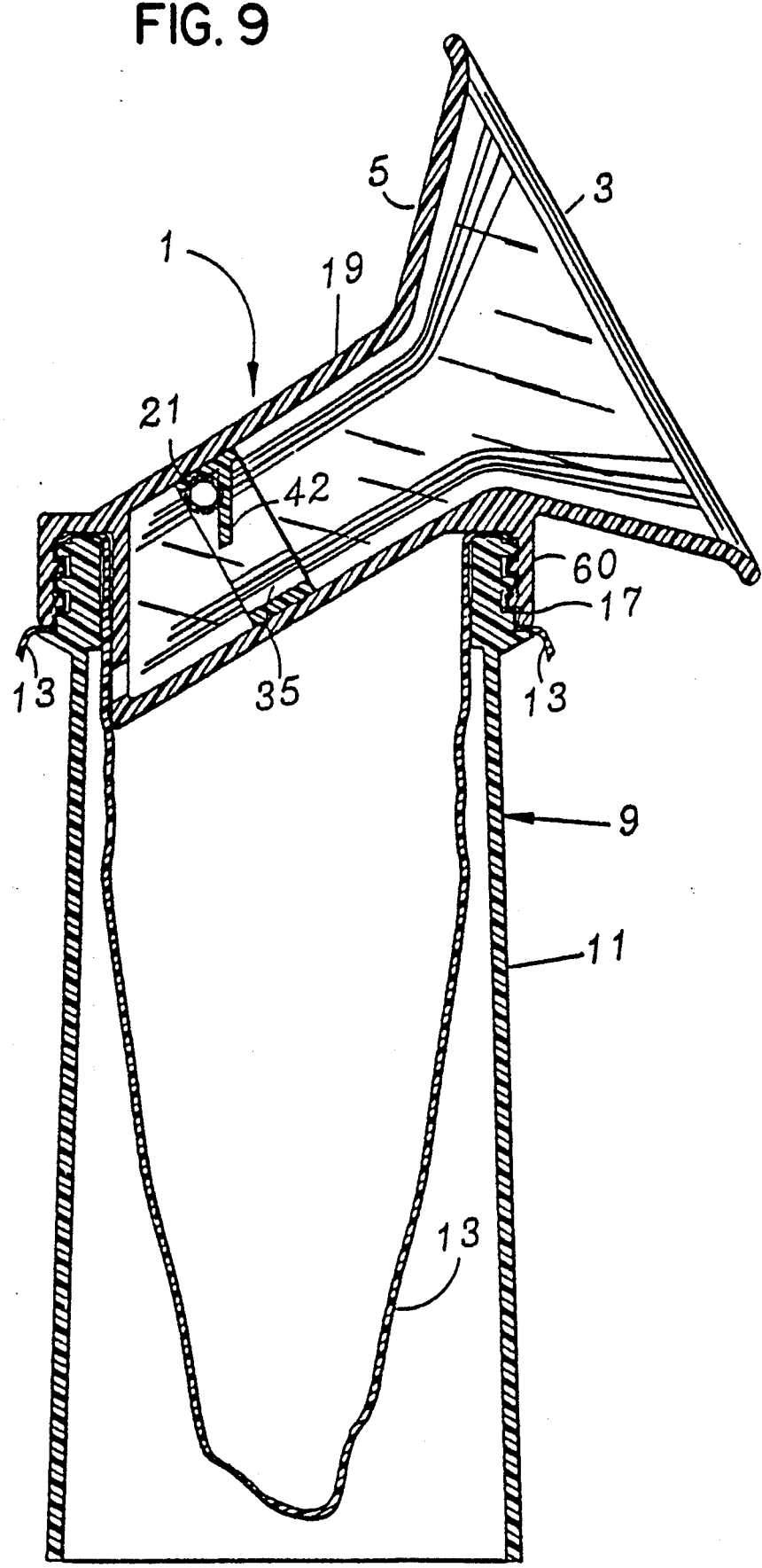
FIG. 9 is a vertical cross-section of the embodiment shown in FIG. 7 installed on a nurser.

In order to prevent the splashing of milk into the pressure inlet 21, a removable baffle 35 shown in FIGS. 2 and 6 may be provided which shields the inlet. The baffle is preferably removable for ease of cleaning. It has a circular plastic ring 43 to which is attached a shield plate 42 which extends to cover about one-half of the diameter of the cylindrical section. The plate 42 is attached at an angle to the ring so that it is roughly parallel to surface 25 when installed. In this way, milk is directed downwardly toward the nurser rather than being splashed back at the breast. The ring 43 has a lower slit to allow flow of milk and to make the circumference flexible, and a hole 48 which aligns with the hole for inlet 21. A thin projecting ridge 49 around the outside edge of hole 48 is aligned to extend into the hole for air inlet 21 and thus holds the baffle in place in the adapter. By making the diameter of the baffle insert slightly greater than the inner diameter of cylindrical section 19, the insert is held in place by friction.

In use, the liner 13 is placed in position in nurser shell 11, the edge of the liner is stretched over threaded end 17 and the nipple-retaining cap 15 is threaded over the threaded end 17 of the shell 11 and the upper edge of liner 13, securing the liner in place. The breast pump, whether electric or manual, is connected to inlet 21 by a hose or other suitable means of connection. Groove 27 is then placed over rim 29 and adapter 1 is snapped into a firm friction fit with the rim 29 by rotating the shield end of the adapter downwardly, bringing resilient clip 23 into contact with the rim 29 and causing it to snap over the rim as the adapter is further pressed down. In this position the cover flanges 40 rest snugly against the upper surface of rim 29 and serve to stabilize the adapter as well as preventing the entry of foreign matter.

The breast may then be positioned within cone 5 for milk extraction. When negative pressure is applied to inlet 21, the flexible liner 13 is drawn against surface 25 and seals hole 31, and milk collects in the lower part of reservoir 40. When positive pressure is applied, liner 13 is forced away from hole 31 and the milk flows into the liner 13. Air is able to be displaced from the liner through opening 41 in flange 40. The seal formed between the liner and surface 25 on the negative pressure stroke is somewhat imperfect, but this is in fact desirable for the breast pump application since too great a period of suction on the breast without relief can rupture the nipple skin. The choice of breast pump used with the adapter will of course determine the length and degree of the negative pressure portion of the cycle.

A similar action takes place where the type of breast pump used does not provide cycles of alternating positive and negative pressure, but rather only intermittent negative cycles. Rather than the milk held in the reservoir 20 being forced through hole 31 on the positive portion of the cycle, the milk simply flows through the hole by gravity when the negative pressure is released.

In the second embodiment of the invention shown in FIGS. 7 through 10, the adapter is moulded in a unitary piece with a threaded circular rim 60. To use this variation of the invention, the liner 13 is placed in position in the nurser shell 11, the edge of the liner is stretched over threaded end 17 and the rim portion 60 of the adapter is threaded down over the edge of the liner to secure the liner for filling. Otherwise, the second embodiment operates in the same manner as the first embodiment.

Figure 12:
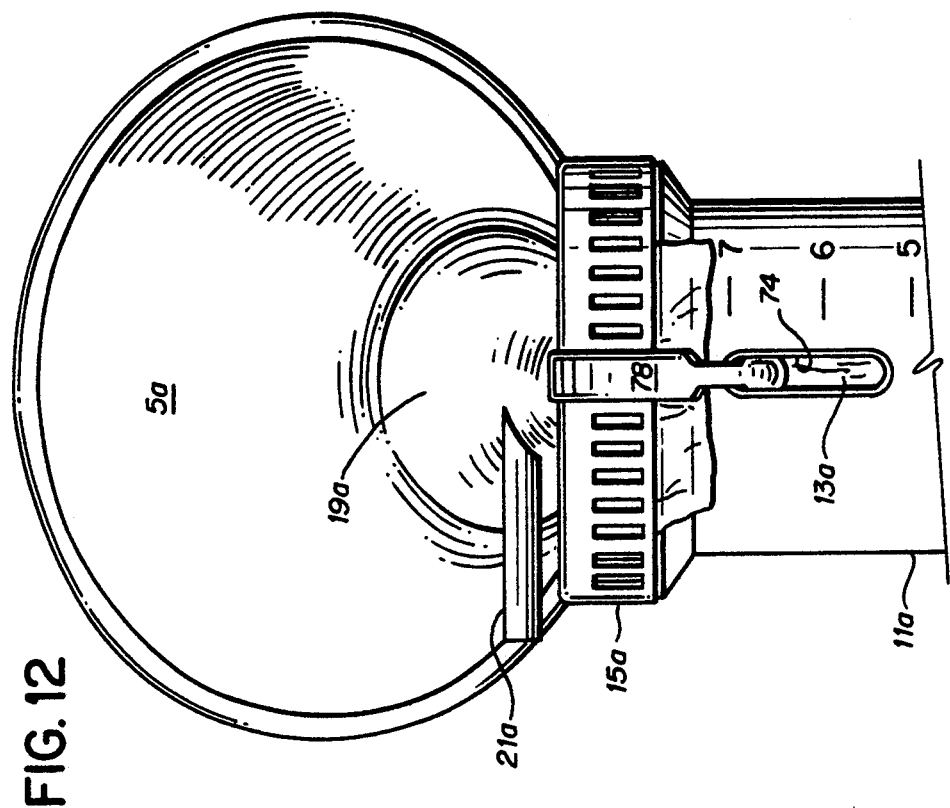
FIG. 12 is a fragmentary rear elevational view thereof looking from left to right in FIG. 11.
Figure 11:
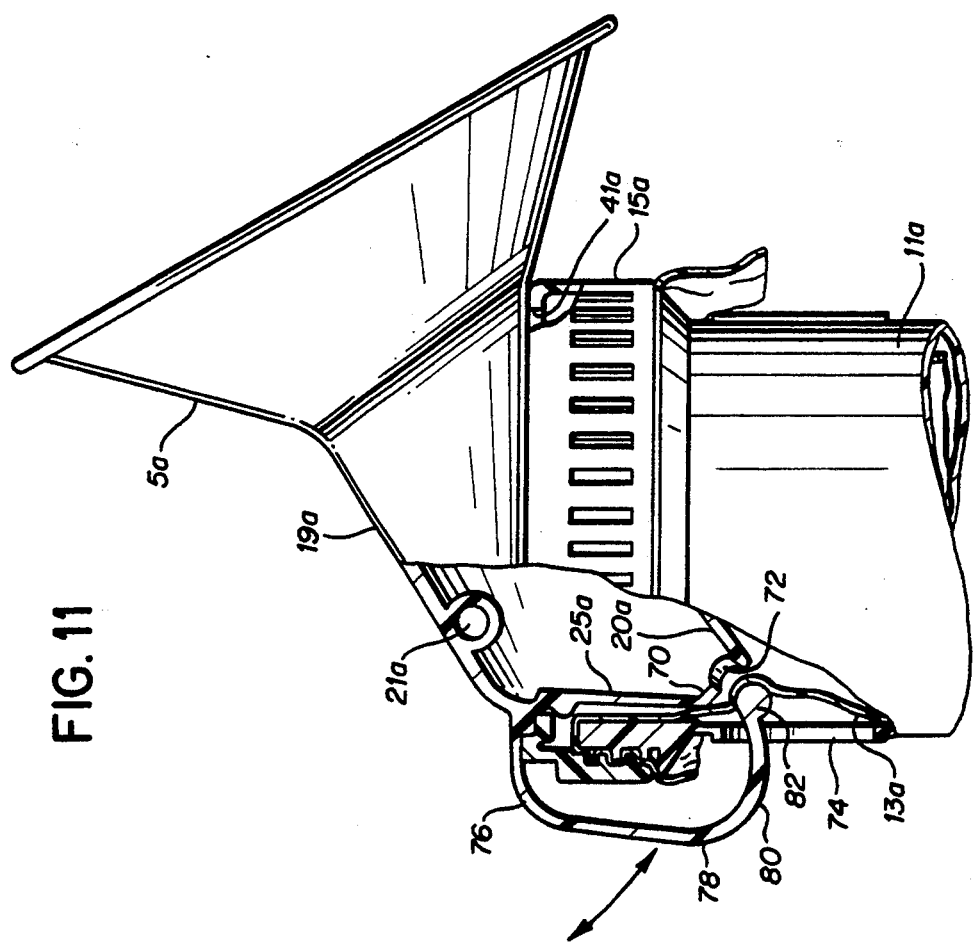
FIG. 11 is a fragmentary side elevational view, with parts broken out and in cross-section, of a further form of adapter mounted on the top of the nurser.

With reference to the embodiments hereof illustrated in FIGS. 11–12, 13–14, 15, 16–17, and 18, respectively, like parts are referenced by like reference numerals followed by the letter suffixes a, b, c, d and e, respectively. In FIGS. 11 and 12, there is illustrated a further embodiment of the breast pump wherein the modulation of the suction is effected by operation of a trigger by the mother. In this form, the adapter has a cylindrical section 19a which forms a lower reservoir section 20a. A connecting tube or air inlet 21a projects generally horizontally from the upper edge of cylindrical section 19a to which a pumping source, not shown, of unmodulated negative pressure is attached. As previously described, the lower end of the reservoir section 20a is substantially closed by a surface 25a and which has a lower end surface 70 which closes the reservoir section 20a. An orifice 72 is formed in the lower end surface 70. The shell 11 of the nurser has two series of slots extending longitudinally through the shell, including an upper slot 74. Along the end surface 25a of the cylindrical section 19a, there is provided a slot, as previously described, for receiving the inner lip of the cap 15a. As in the previously described embodiments, a circular cover flange, not shown, extends horizontally from the cylindrical section 19a and has an aperture 41a in communication with the liner 13a of the nurser to reduce pressure differentials between the interior of the bag or liner and the exterior of the shell.

The adapter illustrated in FIGS. 11 and 12 has a trigger which is actuated by the mother and located externally adjacent the end wall 25a of the adapter. The trigger comprises a generally C-shaped configuration having a relatively thin profile section 76 joining cylindrical section 19a and relatively thicker profile sections 78 and 80, section 78 being adapted for contact by the mother's finger. The lower end of the trigger includes a ball-shaped end 82 disposed adjacent orifice 72.

To use this embodiment, the liner 13a is placed in position in the shell 11a, the edge of the liner being stretched over the threaded end of the shell. The cap 15a is then threaded over the end of the shell, with the upper edge of the liner 13a therebetween securing the liner in place. A suction device is coupled to the tube 21a. The ball-shaped tip 82 of the trigger 76 is received in the slot 74 of shell 11a and is retained between the liner and the shell by the larger diameter of its ball-shaped end relative to slot 74. The trigger 76 is sufficiently resilient to enable the adapter to be snapped into position when the groove becomes engaged with the rim of cap 15a by rotating the shield end of the adapter downwardly. The cap 15a can be distorted to an oval shape and is resilient biased to its circular shape to secure the adapter and cap one to the other. In this position, the flanges of the adapter cover, not shown in these views, rest snugly against the upper surface of the cap rim and serve to stabilize the adapter, as well as to prevent entry of foreign matter.

The breast may then be positioned within the cone 5a of the adapter and a negative pressure is then applied to the reservoir by actuation of the pump. Trigger 76 is then squeezed horizontally toward the nurser and the ball-shaped end 82 of the trigger pivots about the thin sections of the trigger to engage the liner and press the liner against and about orifice 72 to seal the orifice.

As the negative pressure increases within the adapter, milk can flow from the breast into the lower part of the reservoir. If the suction becomes too great or the reservoir becomes full, trigger 76 can be released. The inherent resilience of the trigger draws the ball-shaped end 82 away from orifice 72 to rest against the inner surface of shell 11a at slot 74. The liner falls away from the orifice, enabling the milk from the reservoir to flow into the liner. The alternating cycle of closing and opening the orifice by operation of the trigger is repeated to empty the breast. The ball end 82 and liner 13a thus act as a valve for opening and closing aperture 72 in response to manual actuation of the trigger.

The adapter may be removed for cleaning from the cap 15a by squeezing the cap so as to distort it into an oval shape and releasing the engagement of the cap rim at the groove of the adapter. The adapter can then be canted or tilted relative to the cap to remove it for cleaning purposes.

Figure 13:
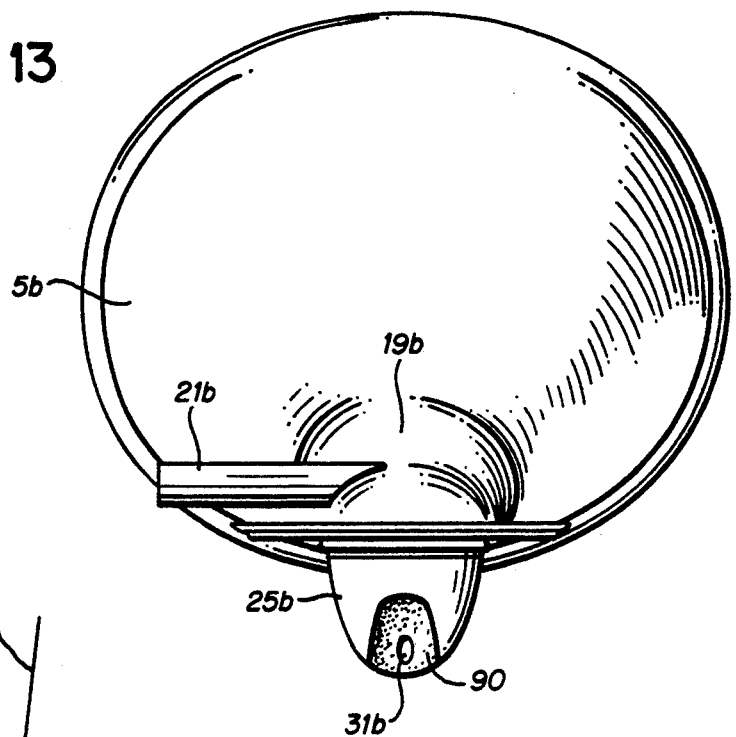
FIG. 13 is a rear elevational view of an adapter according to a further embodiment of the present invention.
Figure 14:
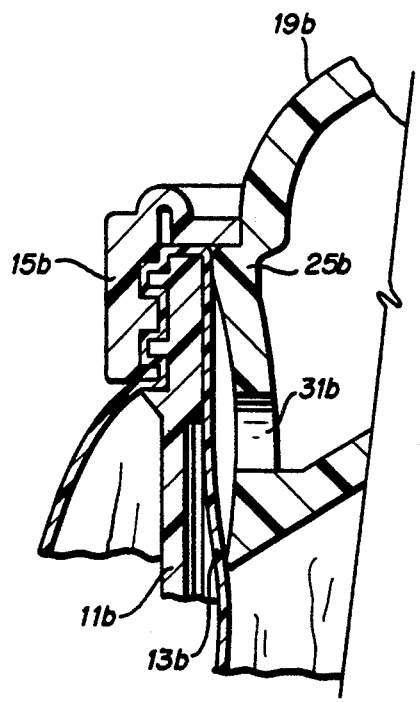
FIG. 14 is a fragmentary enlarged cross-sectional view of the adapter of FIG. 13 mounted in the nurser.

Referring now to the embodiment hereof illustrated in FIGS. 13 and 14, there is illustrated a modification of the convexly curved end wall or surface 25b, as illustrated in the previous embodiments. It will be recalled that the end wall 25 of the reservoir substantially conforms to the circular shape of the neck of the shell with the aperture or orifice opening through that curved wall section whereby milk may be transmitted from the reservoir into the liner. It has been found, however, that substantial positive pressure is necessary to break the surface tension between the liner about the orifice and the wall surface to move the liner away from the hole to permit the reservoir to drain the milk into the liner. This requires a substantial pump displacement and positive pressure within the reservoir. Additionally, with that corresponding curvature of the end wall 25 and the interior neck of the shell, the liner also has to move horizontally from either side of the orifice, which required further additional positive pressure. Pumps capable of this high positive pressure produce radial pleats about the orifice 31 when they reciprocate with negative pressure. These pleats reduce the sealing ability. In the embodiment illustrated in FIGS. 13-14, it has been found possible to reduce those pressure requirements and hence the necessary pump displacement by an improved configuration of the end wall 25 of the reservoir.

In FIGS. 13 and 14, the end wall 25b has a similar circular shape generally conformal to the interior circular wall section of the neck of the shell. However, in the convex outer end wall surface 25b, there is provided a concave portion 90 and in which the aperture or orifice 31b is located for communicating between the reservoir 19b and the interior of liner 13b. Additionally, the aperture 31b is elongated in a vertical direction, and this too facilitates its opening and closing. More particularly, the concave portion 90 has a vertical arc greater than the horizontal arc, the vertical arc being located so that a tangent to the arc at the center of the hole forms an acute angle of about 2° with the shell. By providing the concave portion 90, a sufficient portion of the liner may be flexed inwardly toward the aperture or away from the aperture without horizontal movement of the liner, hence reducing the force necessary to open and close the liner. That is, by locating the liner seal in the area of the concave surface 90, the liner is permitted to readily move toward and away from about the orifice 31b with substantially reduced force. It has been found that this configuration enables a reduction in the pump displacement to about ⅓ of the pump displacement previously necessary for the configuration where the aperture is placed in an end wall of the adapter which conforms to the curvature of the neck of the shell. For example, where a pump displacement of about 13 cubic inches was necessary, it has now been found with the concave portion that a reduction to about 4½ cubic inches of pump displacement is possible. With the version of the adapter illustrated in FIGS. 16 and 17, a pump displacement of even less is possible, for example, on the order of about 3 cubic inches.

Figure 15:
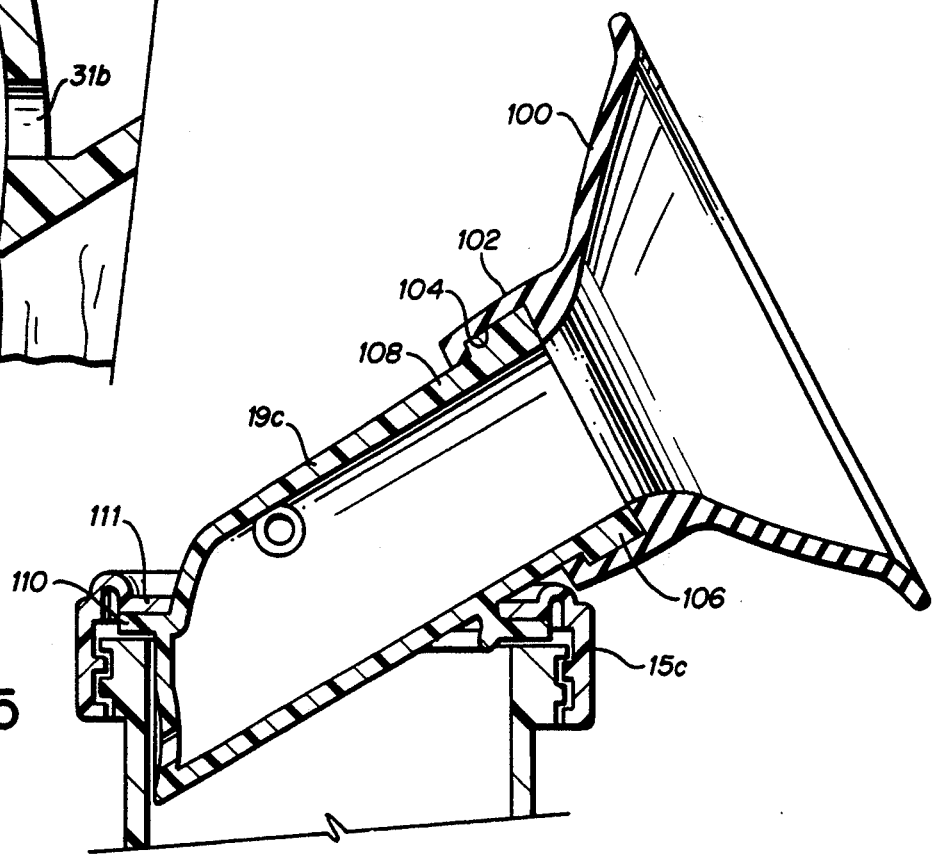
FIG. 15 is a fragmentary cross-sectional view of a further form of the adapter hereof.

Turning now to the embodiment of FIG. 15, it is frequently desirable to provide a more flexible shield than the rigid plastic shield illustrated in the prior embodiments. In this form, a silicone or rubber shield 100 may be provided. Shield 100 is provided with a hub 102 having an internal groove 104 for engaging about a radially outwardly projecting flange 106 formed at the cylindrical end of section 108 of the adapter.

Further, in this form, the adapter may be releasably secured to the nurser between the cap and the neck of the shield. That is, the adapter is provided with a flange 110 formed horizontally about the reservoir 19c of a diameter slightly larger than the diameter of the neck of the shield. Thus, prior to threading cap 15c onto the nurser shell, the adapter, without the flexible shield 100, may be inserted through the cap from its underside with the flange 110 engaging the undersurface of the rim 111 about the cap opening. With that subassembly in place, cap 15c may be threaded about the neck of the shield, clamping the flange 110 of the adapter between the rim and the top of the shield.

Figure 16:
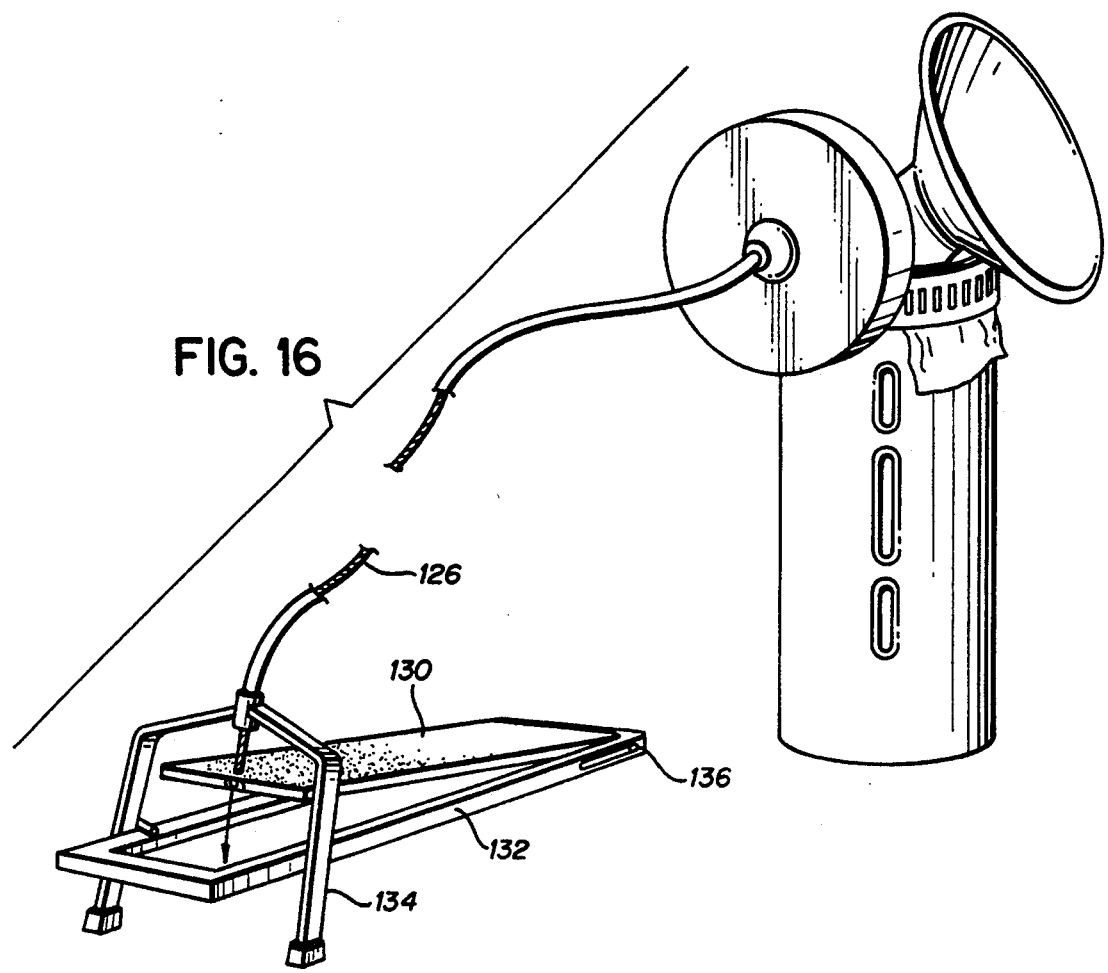
FIG. 16 is a perspective view with parts broken out for clarity of a foot-actuated pump for a further form of adapter according to the present invention.
Figure 17:
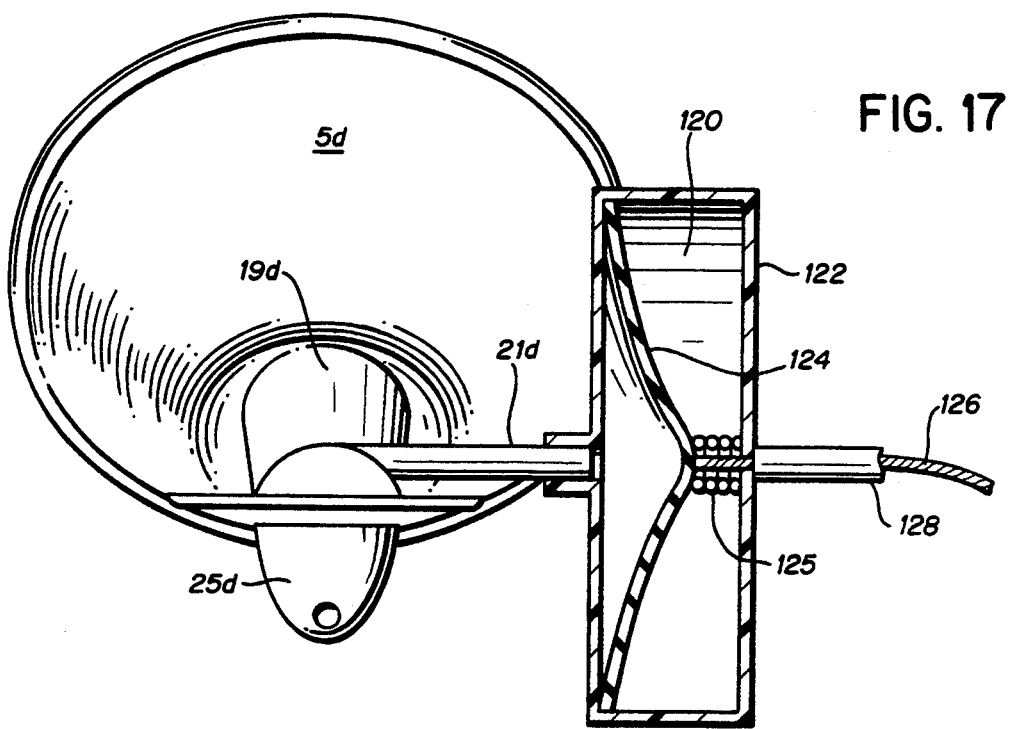
FIG. 17 is a rear and side elevational view of the adapter with parts of the diaphragm valve illustrated in cross-section.

Turning now to the embodiment hereof illustrated in FIGS. 16 and 17, there is provided a breast pump which may be operated by the foot of the mother. In this form, the adapter may, for example, comprise the adapter illustrated in the first embodiment hereof. To the connecting tube 21d, there may be attached a diaphragm pump 120. Pump 120 includes a generally cylindrical housing 122 containing a flexible diaphragm 124 biased for movement by a spring 125 into a flat or disk-like configuration. A central portion of the diaphragm 124 is attached to cable 126 disposed in a sleeve 128. The cable 126 is attached at its opposite end to a pivoted foot pedal 130. The foot pedal 130 forms part of a foot pedal assembly, including a frame 132 which is supported by an inverted U-shaped support 134. The cable 126 is attached to the forward end of foot pedal 130 which is pivoted about a pin 136 at its rear end. Thus, it will be appreciated that up-and-down pivoted movement of the foot pedal 130, in conjunction with spring 125, will displace the diaphragm 124 toward and away from the tube 21d to induce pressure cycles within the reservoir for simultaneously closing the valve, suctioning the breast and then opening the valve to enable milk from the reservoir to flow into the liner.

Figure 18:
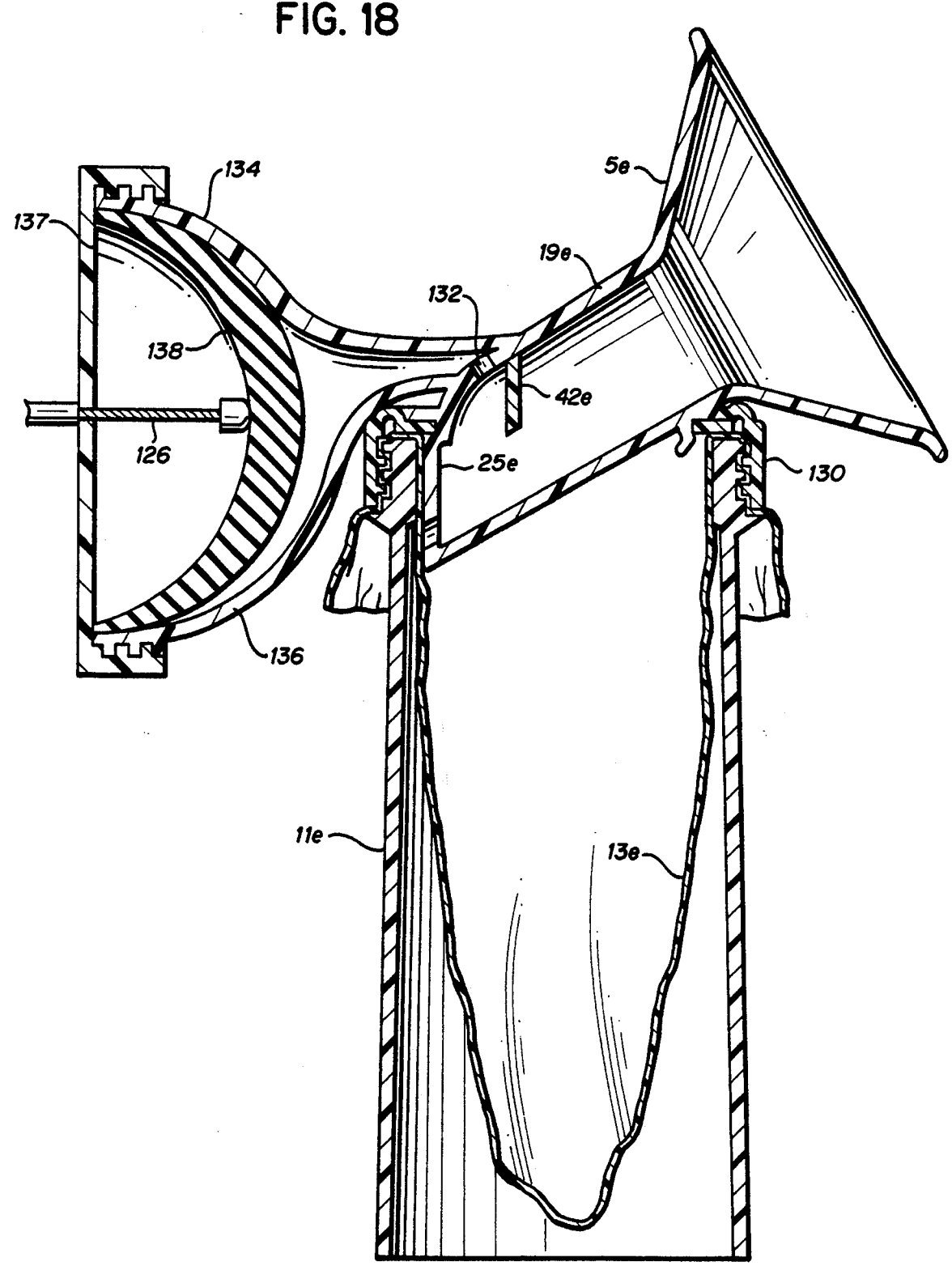
FIG. 18 is an enlarged vertical cross-sectional view through another form of breast pump adapter according to the present invention.

Referring now to FIG. 18, there is illustrated an embodiment hereof wherein there is formed integrally an adapter and a dome-shaped breast pump. Particularly, the adapter includes, preferably as an integral construction of molded plastic material, a breast shield 5e, a reservoir section 19e, an end wall 25e and an internally threaded integral cap portion 130. An aperture 132 for receiving air from a pump 134 is disposed behind a shield plate 42e. The pressure cycles within the reservoir are generated by the pump 134 while shield plate 42e protects the pump and aperture from milk passing through the aperture 132.

The integral pump includes a dome-shaped housing 136 having a generally correspondingly shaped diaphragm 138. Perforated cap 137 connects to the dome housing and supports cable 126 and holds the diaphragm in place. The diaphragm 138 is coupled to the end of a cable 126 or other actuating means whereby the diaphragm 138 can be displaced within the housing 136. The diaphragm 138 is shaped to resiliently return to its dome-shaped condition and displacement: from that position toward the cap 137 inherently biases the diaphragm for return to that dome-shaped configuration and presses the margins of the diaphragm radially outwardly to seal against the housing 136. Upon release of cable 126, the dome-shaped diaphragm is biased toward the illustrated predetermined position. Because of the shape of diaphragm 138 when cable 126 is driven inwardly, the surface adjacent to the perimeter and on the outside of diaphragm 138 is forced against the interior of dome housing 136. Further, the correspondence of the dome-shaped diaphragm and housing reduces the dead air space. Also, cable 126 may be connected at its other end to a transmission which converts the circular motion of an electric motor to reciprocating motion.

Consequently, the embodiment of FIG. 18 provides an adapter with attached pump integrally formed therewith and which may be directly applied to the neck of the shell 11e about the portions of the liner 13e disposed between the neck of the shell and the cap 130. The breast pump hereof accordingly is readily adaptable to the existing shell and liner configuration currently on the market.

Figure 19:
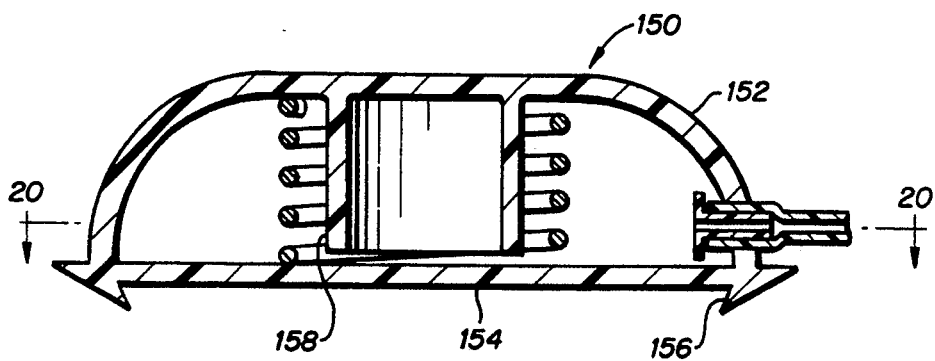
FIG. 19 is an enlarged cross-sectional view of a form of pump for use with the breast pump of the present invention.
Figure 21:
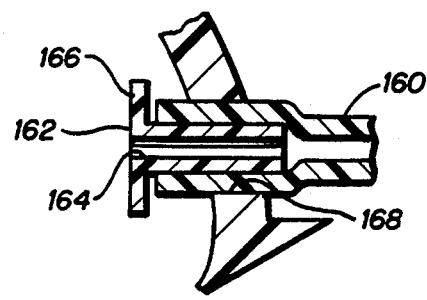
FIG. 21 is an enlarged fragmentary cross-sectional view of a fitting between the pump and an air line to the adapter pump.
Figure 20:
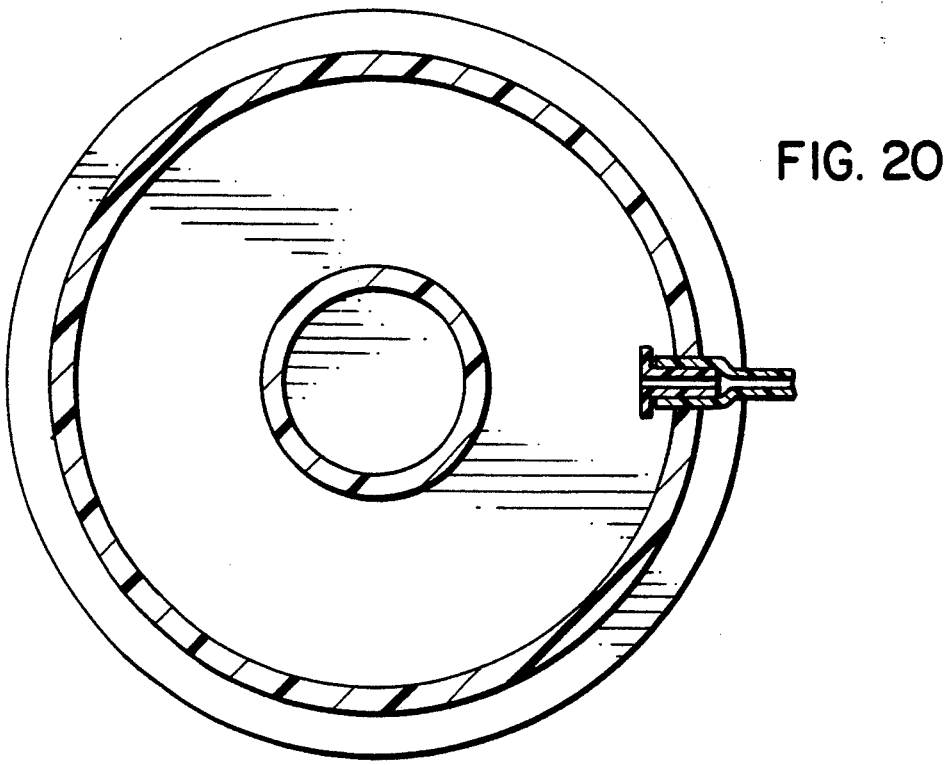
FIG. 20 is a cross-sectional view thereof taken generally about on line 20—20 in FIG. 19.

FIGS. 19-21 illustrate a preferred pump 150 for connection with the opening or aperture 21 of the adapter 1. Pump 150 includes a generally hemispherical or dome-shaped element 152 and a circular cap 154. The dome-shaped element 152 is open along its underside and the cap 154 is releasably coupled to element 152 by a flexible retaining rim 156 projecting inwardly from the lower edge of element 152. Element 152 includes a generally cylindrical or annular member 158 projecting downwardly from the apex of the dome toward, but terminating short of the cap 154. The dome 152, cap 154 and annular element 158 are formed of flexible materials responsive to foot pressure or other manually applied pressure to change the volume within the pump 150.

A tube 160, preferably formed of plastic material, is connected at one end to the fitting defining opening or aperture 21 of the breast pump adapter, as illustrated in FIG. 1. The opposite end of the tubing is enlarged and receives a pin 162 having a bore 164 therethrough. The pin 162 also includes a radially extending flange 166 larger in diameter than the diameter of the opening 168 through a side portion of the dome-shaped element 152. The pin 162 enlarges the end of the tube 160 to frictionally retain the tube 160 in the opening 168 in dome member 152. The flange 166 serves to prevent the tube 160 from being pulled outwardly away from element 152.

In use, it will be appreciated that the individual operating the pump may simply press the top portion of the dome-shaped element 152 toward cap 154 to increase the pressure within the volume of the pump, thereby increasing the pressure within the chamber of the adapter via tube 160. Because of the flexible resilient nature of the dome-shaped element 152, a relaxation of foot or other manual pressure on element 152 permits the element 152 to return to its original shape, lowering the pressure within the volume, thereby causing a reduced pressure in the chamber of the breast pump adapter via tube 160. The cylindrical portion 158 serves a dual purpose. First, it assists the return of the dome-shaped element 152 to its original position once having been depressed to provide a positive pressure within the breast pump adapter. Secondly, the annular shape of the cylindrical element 158 permits the tube 160, when the cap 154 is removed, to be withdrawn and coiled within the dome-shaped element 152 and about the cylindrical element 158. Thus, with the cap reapplied to the dome-shaped element 152 and the tube coiled within the pump, there is provided an efficient storage mechanism for the tube for storage and transportation of the breast pump adapter when not in use.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of filling an infant nurser including a rigid shell and a flexible liner within said shell romping a container for storing milk and employing an adapter having a chamber in the adapter in communication with a breast shield, and a passage through said adapter for communication between said chamber and said flexible container, comprising the steps of:

applying a first pressure within the chamber in communication with a female breast through the breast shield for expressing milk from the breast into the chamber in response to the application of said first pressure in said chamber, the step of applying said first pressure including applying a negative suction to said chamber to draw a portion of said flexible liner against said adapter to seal said passage;

applying a second pressure within said chamber higher than said first pressure to displace the flexible liner portion away from said adapter to enable flow of milk from said chamber through said passage into the flexible container;

temporarily storing in said chamber the milk expressed during application of said first pressure;

flowing the milk from said chamber into said flexible container during application of said second pressure; and alternating the pressure applied to said chamber between said first and second pressures.

2. A method according to claim 1 wherein the passage includes an aperture in a wall in part defining said chamber, the step of applying said first pressure including applying a negative suction to said chamber to draw a portion of said flexible liner about the margins of said aperture to seal said aperture, said second pressure being a positive pressure for extending the flexible liner portion away from the adapter to open the passage through said adapter.

3. A method according to claim 1 including the steps of closing said passage in response to application of said first pressure to said chamber to isolate the flexible container and chamber from one another and enable the milk to be temporarily stored in said chamber, and opening said passage in response to application of said second pressure to said chamber to enable flow of the milk from said chamber to said flexible container.

4. A method according to claim 1 including the step of isolating the nurser from the chamber during the application of said first pressure.

5. A method according to claim 2 including the step of isolating the nurser from the chamber during the application of said first pressure.

6. A method according to claim 1 wherein the first and second pressures are applied by a foot-actuated pump, the step of applying said first pressure including displacing a foot-actuated member to operate said pump.

7. Apparatus for filling infant nursers comprising:
an infant nurser having a rigid shell and a flexible, liquid-containing liner supported in said rigid shell;
an adapter including a breast shield adapted to receive a female breast;
means defining a hollow chamber in communication at one end with said shield and substantially closed at its opposite end, said chamber-defining means having a wall portion with an aperture through the wall portion for the passage of milk from the chamber into said liner;
means carried by said adapter for connecting a pump in communication with said hollow chamber to produce alternating pressures within said chamber;
means carried by said adapter for releasably securing said adapter to said nurser and relative to said flexible liner supported in said nurser whereby said wall portion is placed in sufficiently close proximity to a portion of said flexible liner to cause said liner portion to act as a valve with respect to said aperture, said wall portion including a concave portion about said aperture and in opposition to the liner for facilitating movement of the liner portion toward said aperture into said concave portion to seal the aperture and away from said aperture outwardly of said concave portion to open the aperture in response to the alternating pressures within said chamber; and
said shell having an end portion, said securing means including a threaded cap about said end portion of said shell securing said liner between said shell and said cap with the liner disposed within the shell end portion, said wall portion including a convex portion in general conformance to the curvature of said shell, said concave portion being disposed in said convex portion.

8. Apparatus according to claim 7 wherein said cap has a central opening forming an inner annular lip and said securing means comprises a horizontal groove in said adapter for releasably securing said adapter to said lip of said cap.

9. An adapter as part of a breast pump for filling infant nursers wherein the infant nurser comprises a flexible, liquid-containing liner supported in a rigid shell, the adapter comprising:
a breast shield adapted to receive a female breast;
means defining a hollow chamber in communication at one end with said shield and substantially closed at its opposite end, said chamber-defining means having a wall portion with an aperture through the wall portion for the passage of milk from the chamber into the liner;
means carried by said adapter for connecting a pump in communication with said hollow chamber to produce alternating pressures within said chamber; and
means carried by said adapter for releasably securing said adapter to the nurser and relative to a flexible liner supported in the nurser whereby said wall portion is placed in sufficiently close proximity to a portion of said flexible liner to cause said liner portion to act as a valve with respect to said aperture, said wall portion including a concave portion about said aperture and in opposition to the liner shell for facilitating movement of the liner portion toward said aperture into said concave portion to seal the aperture and away from said aperture outwardly of said concave portion to open the aperture in response to the alternating pressures within said chamber.

10. An adapter according to claim 8 wherein said shield is formed of a flexible material.

11. An adapter according to claim 10 wherein said shield is releasably secured to said chamber defining means.

12. An adapter according to claim 7 including a pump in communication with said hollow chamber, said pump being a foot-actuated pump, having a member movable to actuate said pump in response to force applied to said member by a foot.

13. An adapter as part of a breast pump for filling infant nursers wherein the infant nurser comprises a flexible, liquid-containing liner supported in a rigid shell, the adapter comprising:
a breast shield adapted to receive a female breast;
means defining a hollow chamber in communication at one end with said shield and substantially closed at its opposite end, said chamber-defining means having a wall portion with an aperture through the wall portion for the passage of milk from the chamber into the liner;
means carried by said adapter for connecting a pump in communication with said hollow chamber to produce a negative pressure within said chamber;
means carried by said adapter for releasably securing said adapter to the nurser and relative to a flexible liner supported in the nurser whereby said wall portion is placed in sufficiently close proximity to a portion of said flexible liner to serve in conjunction with said liner portion as a valve with respect to said aperture; and
a manual actuator carried by said adapter for actuating said valve.

14. An adapter according to claim 13 wherein said actuator includes a valve closure element movable in response to movement of said actuator into a position for closing the liner portion into sealing engagement about said aperture.

15. An adapter according to claim 13 wherein said shield is formed of a flexible material.

16. An adapter according to claim 15 wherein said shield is releasably secured to said chamber-defining means.

17. An adapter according to claim 13 including a pump in communication with said hollow chamber, said pump being a foot-actuated pump having a member movable to actuate said pump in response to force applied to said member by a foot.

18. Apparatus for filling infant nursers comprising:
an infant nurser having a rigid shell and a flexible, liquid-containing liner supported in said rigid shell;
an adapter including a breast shield adapted to receive a female breast;

means defining a hollow chamber in communication at one end with said shield and substantially closed at its opposite end, said chamber-defining means having a wall portion with an aperture through the wall portion for the passage of milk from the chamber into said liner:

means carried by said adapter for connecting a pump in communication with said hollow chamber to produce pressures of different magnitudes within said chamber;

means carried by said adapter for releasably securing said adapter to said nurser and relative to said flexible liner supported in said nurser whereby said wall portion is placed in sufficiently close proximity to a portion of said flexible liner to cause said liner portion to act as a valve with respect to said aperture, said wall portion including a concave portion about said aperture and in opposition to the liner for facilitating movement of the liner portion toward said aperture into said concave portion to seal the aperture and away from said aperture outwardly of said concave portion to open the aperture in response to the pressures of different magnitudes within said chamber;

an actuator including a valve closure element movable in response to movement of said actuator into a position for closing the liner portion into sealing engagement about said aperture; and said shell having an end portion, said securing means including a threaded cap about said end portion of said shell securing said liner between said shell and said cap with the liner disposed within the shell end portion.

19. Apparatus according to claim 18 wherein said cap has a central opening forming an inner annular lip and said securing means comprises a horizontal groove in said adapter for releasably securing said adapter to said 1lip of said cap.

20. Apparatus according to claim 18 wherein said breast shield, said hollow chamber de:fining means and said securing means comprise an integral, one-piece construction.

21. An adapter as part of a breast pump for filling an infant nurser in combination with the infant nurser, comprising:

a rigid shell having an open end;

a flexible liner for containing a liquid and supported within said rigid shell about said open end;

a breast shield carried by said adapter for receiving a female breast;

means carried by said adapter defining a hollow chamber in communication at one end with said shield and substantially closed at its opposite end, said chamber-defining means having a wall portion with a passage through the wall portion for passing liquid from the chamber into the liner;

a pump including a housing and a member movable relative to said housing defining at least in part an expandable and contractable volume within said housing, said volume being in communication with said chamber, means for displacing said member relative to said housing for producing alternating pressures within said chamber;

a valve for opening and closing said passage in response to said alternating pressures within said chamber; and means carried by said adapter for releasably securing said adapter to said shell adjacent said open end thereof, said adapter and said liner being located relative to one another such that said wall portion and a portion of said flexible liner are located in sufficiently close proximity to one another to cause said flexible liner portion to act as said valve with respect to said passage.

22. The combination according to claim 21 wherein said displacing means includes a manual actuator including a frame, a foot pedal carried by said frame for movement and a cable connected at one end to said foot pedal and at its other end to said member for displacing said member in response to movement of said foot pedal.

23. The combination according to claim 21 wherein said securing means includes a threaded cap about said end portion of said shell securing said liner between said shell and said cap with the liner disposed within the shell end portion.

24. The combination according to claim 21 wherein said shield is formed of a flexible material.

25. The combination according to claim 24 wherein said shield is releasably secured to said chamber-defining means.

26. The combination according to claim 21 wherein said adapter and said pump are integrally formed of a plastic material.

27. A breast pump in combination with an infant nurser comprising:

a generally cylindrical shell having an externally threaded neck portion;

a flexible liner disposed in said shell with portions overlapping the neck portion of said shell and the externally threaded portion thereof;

an adapter as part of the breast pump for filling said liner with milk including a breast shield adapted to receive a female breast and an opening in said adapter for discharging milk from the adapter into said liner;

means including an internally threaded part for cooperation with the externally threaded neck of said shell for releasably securing the adapter, shell and liner to one another;

means in communication with said chamber for periodically changing the pressure in said chamber; and a valve for opening and closing said opening in response to the changing pressure in said chamber, said adapter opening being located relative to said liner within said shell such that a wall portion of said adapter about said opening is placed in sufficiently close proximity to said flexible liner to cause a portion of said liner to act as a portion of said valve with respect to said adapter opening whereby said liner portion and said wall portion cooperate to open and close said adapter opening.

28. Apparatus for expressing milk from a female breast and storing the milk to facilitate the nursing of an infant, comprising:

a generally cylindrical shell having an externally threaded neck portion;

a flexible liner disposed in said shell with portions overlapping the neck portions of said shell and the external threads thereof;

an adapter for filling said liner with milk including a breast shield adapted to receive a female breast and an opening in said adapter for discharging milk from the adapter into said liner;

said flexible liner and said adapter being cooperable with one another for modulation of milk expression and storage within said apparatus; and means including an internally threaded part for cooperation with the externally threaded neck of said shell for releasably securing the adapter, shell and liner one to the other;

said securing means including a collar carrying said internally threaded part.

29. Apparatus according to claim 28 wherein said collar has a central opening defined by a rim, said adapter having means cooperable with said rim enabling said adapter for releasable engagement with said collar; and a chamber in said adapter in communication with said breast shield and said discharge opening, a pump periodically changing the pressure in said chamber, a valve including a portion of said flexible liner responsive to said changing pressure in said chamber for alternately enabling the milk received from the breast shield to be stored in said chamber and flowing the milk from the chamber into said liner, said adapter being removable from said collar to enable a nursing nipple to be applied to the collar.

30. Apparatus according to claim 29 wherein said cooperable means enables said adapter for snap-in engagement with said collar.

31. Apparatus according to claim 30 wherein said adapter has a groove for receiving said rim and a flexible catch for engaging below said rim.

32. Apparatus according to claim 29 wherein said pump is a foot-actuated pump having a member movable to actuate said pump in response to force applied to said member by a foot.

33. Apparatus according to claim 29 including a foot-operated pump for alternately pressurizing said chamber, the foot-operated pump including a generally dome-shaped element having an internal reel and a tube in communication between said chamber and the volume within the dome-shaped element, said tube being coilable about said reel for storing said tube within the pump.

34. Apparatus according to claim 28 wherein said breast shield and said collar carrying said internally threaded part are integral one with the other.

35. Apparatus according to claim 34 including a chamber in said adapter in communication with said breast shield and said discharge opening, a pump for periodically changing the pressure in said chamber, a valve including a portion of said flexible liner responsive to said changing pressure in said chamber for alternately enabling the milk received from the breast shield to be stored in said chamber and flowing the milk from the chamber into said liner.

36. Apparatus according to claim 28 wherein said shell includes an opening through said neck portion, said adapter including a generally radially projecting flange for overlying said neck portion, said collar overlying said adapter flange such that, when the adapter is secured to said shell, said flange is clamped between said collar and said neck portion to said shell.

37. Apparatus according to claim 36 wherein said adapter includes an adapter body, said breast shield being releasably secured to said adapter body, said collar having a flange defining an opening through said collar for receiving a portion of said adapter body from the underside of said collar for engaging said adapter flange against the underside of said collar flange.

38. Apparatus for expressing milk from a female breast and storing the milk to facilitate the nursing of an infant, comprising;

a generally cylindrical shell having an externally threaded neck portion;

a flexible liner disposed in said shell with portions overlapping the neck portions of said shell and the external threads thereof;

an adapter for filling said liner with milk including a breast shield adapted two receive a female breast and an opening in said adapter for discharging milk from the adapter into said liner;

means including an internally threaded part for cooperation with the externally threaded neck of said shell for releasably securing the adapter, shell and liner one to the other;

said securing means including a collar carrying said internally threaded part;

said adapter having a body including said opening and a wall portion including a concave portion about said opening, said opening lying generally centrally of said concave wall portion, means for periodically changing the pressure in said chamber, and a flexible element carried by said apparatus for movement toward and into engagement with said concave wall portion to seal said opening and away from and out of engagement with said concave wall portion to open said opening in response to the alternating pressures within said chamber.

39. Apparatus according to claim 38 wherein said breast shield and said collar carrying said internally threaded part are integral one with the other.

40. Apparatus according to claim 38 wherein said collar is rotatable relative to said adapter to secure said adapter and said shell one to the other.

41. Apparatus for filling infant nursers comprising:

an infant nurser having a rigid shell and a flexible, liquid-containing liner supported in said rigid shell;

an adapter including a breast shield adapted to receive a female breast;

means defining a hollow chamber in communication at one end with said shield and substantially closed at its opposite end, said chamber-defining means having a wall portion with an aperture through the wall portion for the passage of milk from the chamber into said liner;

means carried by said adapter for connecting a pump in communication with said hollow chamber to produce alternating pressures within said chamber;

means carried by said adapter for releasably securing said adapter to said nurser and relative to said flexible liner supported in said nurser whereby said wall portion is placed in sufficiently close proximity to a portion of said flexible liner to cause said liner portion to act as a valve with respect to said aperture;

a manually operable actuator including a valve closure element movable in response to movement of said actuator to close the liner portion into sealing engagement about said aperture and to enable movement of said liner portion away from said aperture to open said aperture; and said shell having an end portion, said securing means including a threaded cap for threaded engagement about said end portion of said shell securing said liner between said shell and said cap with the liner disposed within the shell end portion.

42. Apparatus according to claim 41 wherein said breast shield, said hollow chamber defining means and said securing means comprise an integral, one-piece construction.

* * * * *